United States Patent [19]

Davis et al.

[11] 4,267,769
[45] May 19, 1981

[54] PREFABRICATED KNOCKDOWN CLEAN ROOM

[75] Inventors: George B. Davis, Frederick; Robert W. Irving, Boonsboro, both of Md.

[73] Assignee: Environmental Air Control, Inc., Hagerstown, Md.

[21] Appl. No.: 14,177

[22] Filed: Feb. 22, 1979

[51] Int. Cl.³ .......................................... B01D 50/00
[52] U.S. Cl. ............................... 98/33 A; 55/385 A; 55/DIG. 29; 52/578
[58] Field of Search ............. 128/1 R; 98/33 A, 33 R, 98/36, 115 LH; 55/385 A, DIG. 18, DIG. 19, DIG. 29; 52/578

[56] References Cited

U.S. PATENT DOCUMENTS

| | | | |
|---|---|---|---|
| 3,115,819 | 12/1963 | Mahlmeister | 55/DIG. 29 |
| 3,273,323 | 9/1966 | Whitfield | 55/385 |
| 3,611,907 | 10/1971 | Wasserman | 98/33 |
| 3,638,404 | 2/1972 | Moll et al. | 55/473 |
| 3,680,273 | 8/1972 | Bigelow | 52/143 |
| 3,707,811 | 1/1973 | Hampson | 52/23 |
| 3,897,721 | 8/1975 | Fuhst | 98/115 LH |
| 3,986,850 | 10/1976 | Wilcox | 55/385 A |
| 4,074,475 | 2/1978 | Wahlquist | 52/70 |

FOREIGN PATENT DOCUMENTS 2356780 5/1975 Fed. Rep. of Germany .......... 98/36

OTHER PUBLICATIONS

Environmental Air Control, *Clean Labs and Rooms Pre-Fabbed Custom Modular Installations.* 1973.
Bio Clean, *Bioclean Pathogen-Free-Air Systems*, 1972.
Bio Clean, *Portable Laminar Air-Flow Enclosure*, 1975.

*Primary Examiner*—Henry C. Yuen
*Assistant Examiner*—Henry Bennett
*Attorney, Agent, or Firm*—Dowell & Dowell

[57] ABSTRACT

An apparatus for providing a prefabricated knockdown clean room which may be readily assembled without tools in a minimum of time. The apparatus includes a plurality of building segments which cooperate with each other in assembled relationship and certain of such segments include means for moving air under pressure through a filter media which removes substantially all micro-organisms from the air within the apparatus to supply Class 100 air to a restricted area.

3 Claims, 10 Drawing Figures

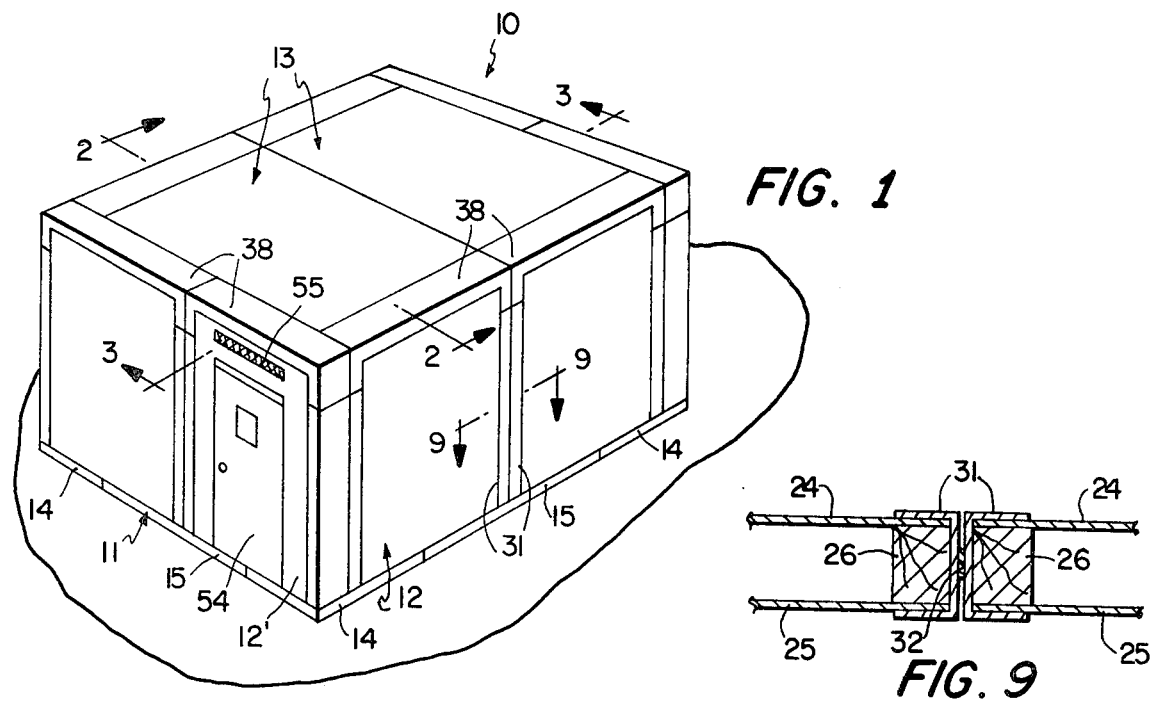
FIG. 1
FIG. 9
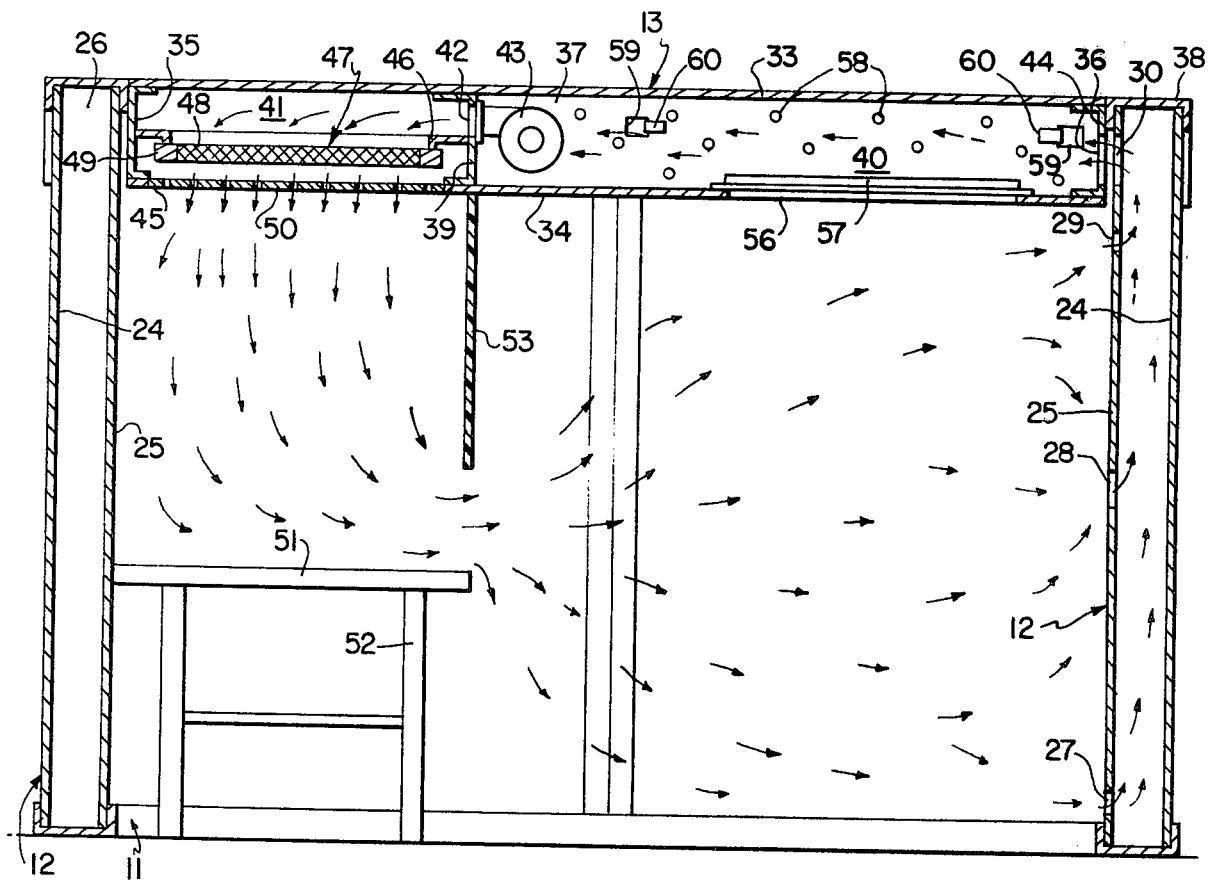
FIG. 2

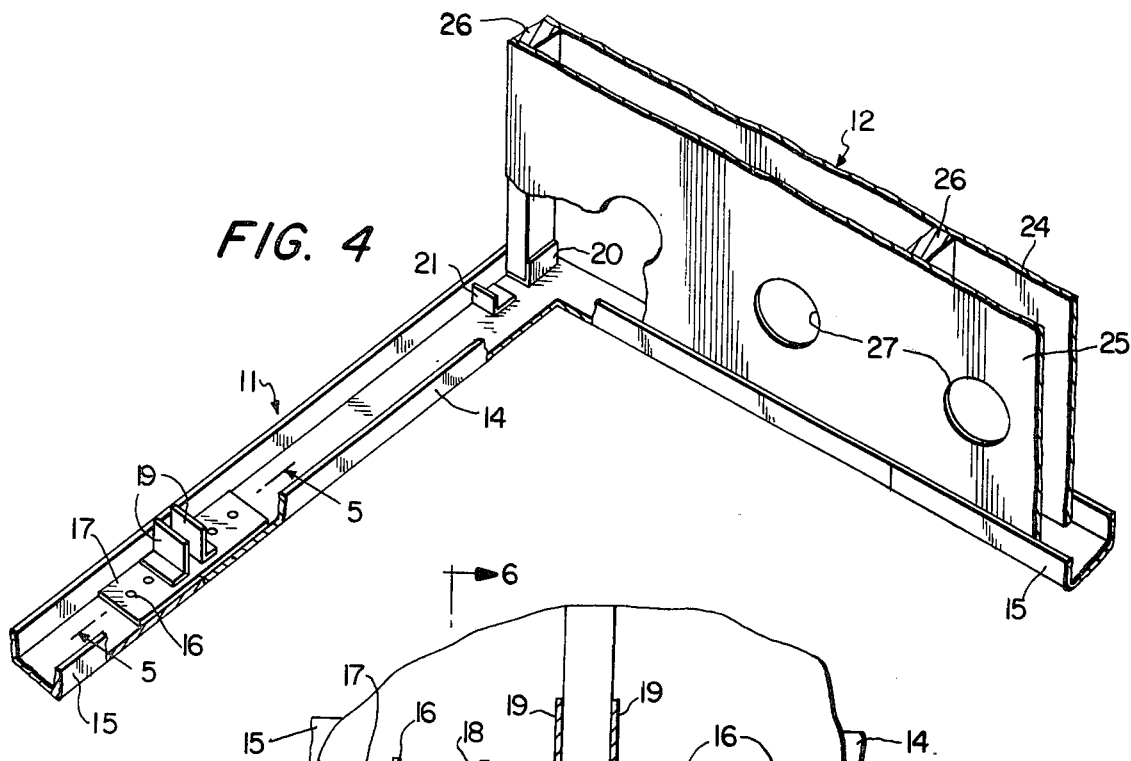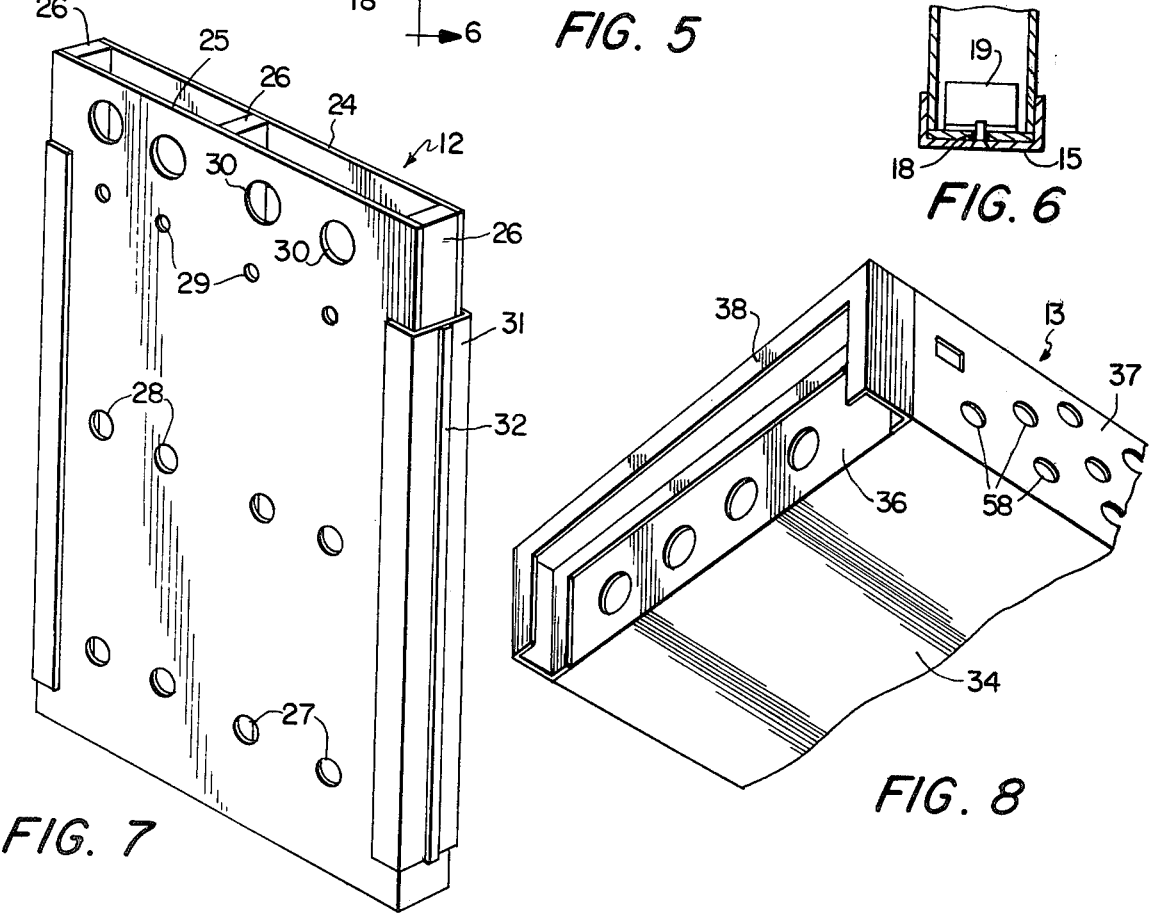

PREFABRICATED KNOCKDOWN CLEAN ROOM

BACKGROUND OF THE INVENTION

In the past, many establishments, such as scientific laboratories, micro-electronic manufacturers, testing labs, hospitals, and the like, have required relatively clean air from which substantially all dust particles, micro-organisms, and pathogens have been removed. Normally atmospheric air contains many thousands of particles per cubic foot and due to air filtering systems certain classifications of air have been established. For example, Class 10,000 indicates that there are 10,000 or less particles of a size 0.5 micron and larger in one cubic foot of air and Class 100 indicates that there are 100 or less particles of a size 0.5 micron and larger in one cubic foot of air. Even though filters have been developed which can remove substantially all of the particles and micro-organisms from the air, it has been difficult to maintain the air in a clean room at a desired level due to the people who are in the room, as well as the necessity for providing ingress and egress to the room. In some cases, such as in the manufacture of micro-electronic parts, a yield rate of 30% has been acceptable. In order to improve the maintaining of clean air in a clean room, special permanent structures have been designed and built using laminar airflow and recirculation paths for the air and the people who are located in the clean room have worn non particle generating lab coats and in some instances have worn non particle generating gloves, boots, hats and masks.

SUMMARY OF THE INVENTION

The present invention is embodied in a plurality of prefabricated knockdown building segments which may be easily assembled by two people without tools in a minimum of time and with minimum effort. The segments include base members, side wall sections, and roof sections which may be assembled in a floor plan of any desired configuration including generally square, rectangular, L-shaped, U-shaped and the like. Certain of the segments may be prewired in a manner such that one segment may be electrically connected to an adjacent segment so that the completed structure may be connected to a single main breaker panel. Each of the roof sections includes top and bottom panels which define an overhead compartment and a transverse partition separates such compartment into a plenum chamber and an air return chamber. A blower is mounted on the partition and such blower forces air from the air return chamber through an opening in the partition into the plenum chamber. The side wall sections have inner and outer panels with some of the inner panels having a plurality of openings or vents which permit air to flow from the interior of the structure through the wall section and into the air return chamber. The bottom panel of the plenum chamber includes an opening within which a filter is mounted in such a manner that all of the air within the plenum chamber must pass through the filter. Such filter removes approximately 99.97% of the micro-organisms from the air. A distribution panel is located below the filter and such distribution panel includes a multiplicity of perforations which permit the air to flow therethrough in a non-aspirating turbulence free flow. Within the structure, means is provided for circulating the flow of clean air over a work surface and then past one or more operators, after which the air flows through the structure to the vents in the wall section and then to the air return chamber.

It is an object of the invention to provide a prefabricated knockdown clean room including a plurality of building segments which may be easily assembled in a minimum of time and with minimum effort and which provides a self-contained environment after the sections have been assembled, as well as a structure which will provide a pure Class 100 air in a non-aspirating turbulence free flow over a work surface.

Another object of the invention is to provide a prefabricated clean room which supplies clean air to a restricted area regardless of any leakage of outside air into the room.

BRIEF DESCRIPTION OF THE DRAWINGS

FIG. 1 is a perspective view illustrating one application of the invention in assembled relationship.

FIG. 2 is an enlarged sectional view taken on the line 2—2 of FIG. 1.

FIG. 4 is an enlarged fragmentary perspective view illustrating one corner of the housing.

FIG. 5 is an enlarged sectional view taken on the line 5—5 of FIG. 4.

FIG. 6 is a sectional view taken on the line 6—6 of FIG. 5.

FIG. 7 is a perspective view illustrating one of the side wall segments.

FIG. 8 is a fragmentary bottom perspective view of one end of a roof segment.

FIG. 9 is an enlarged sectional view taken on the line 9—9 of FIG. 1.

DESCRIPTION OF THE PREFERRED EMBODIMENT

Figure 3:
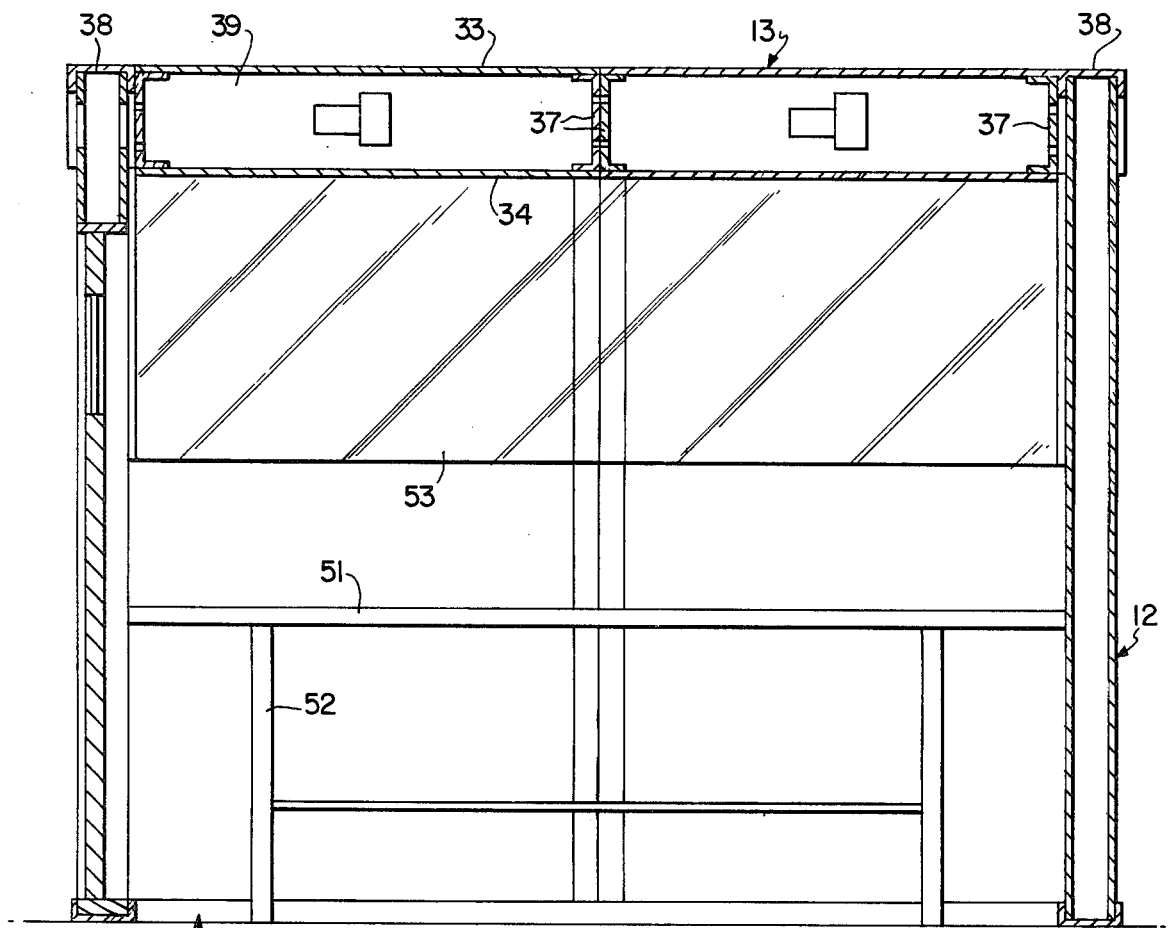
FIG. 3 is an enlarged sectional view taken on the line 3—3 of FIG. 1.

With continued reference to the drawings, a prefabricated knockdown clean room 10 is provided including a base 11 on which a plurality of side wall sections 12 are mounted and such side wall sections support a plurality of roof sections 13. As illustrated best in FIG. 4, the base 11 includes a plurality of corner members 14 each of which includes a pair of generally U-shaped channel members or legs that are welded or otherwise attached to each other at right angles. Each leg of the corner member 14 is longitudinally aligned in end-to-end relationship with an elongated U-shaped intermediate member 15 which is located adjacent thereto. Each of the U-shaped corners and intermediate members of the base 11 includes a web or bight portion having upstanding flanges along each side.

In order to connect the corner member 14 to the intermediate member 15 in a manner to prevent spreading apart, at least one upstanding pin or post 16 is provided adjacent to the end of each leg of the corner member 14 and at least one upstanding pin or post 16 is provided adjacent to each end of the intermediate member 15. A tie plate 17 having a width substantially equal to the width of the web portions of the corner member and the intermediate member is provided having openings 18 which are spaced apart a distance corresponding to the distance between the pins 16 when the base members are in substantially abutting relationship. If desired, the upper portions of the pins 16 may be threaded to receive a conventional nut, or such pins could be unthreaded and adapted to receive a mechanical fastener such as a "speed nut" or the like. Also, it is noted that the openings of the tie plate 17 could merely receive the ends of the pins 16 and not be fastened thereto since the tie plates are primarily to prevent spreading apart of the base members.

A pair of spaced angle members 19 are welded or otherwise attached to the tie plate 17 in parallel relationship with each other and generally normal to the longitudinal axis of the tie plate for a purpose which will be described later. An angle member 20 is welded or otherwise attached to the corner member 14 adjacent to the corner and generally normal to the longitudinal axis of one of the legs. Another angle member 21 is welded or otherwise attached to the corner member adjacent to the angle member 20 and the angle member 21 is positioned generally normal to the other leg of the corner member. Each of the angle members 20 and 21 has a length less than the width of the web portion of the U-shaped corner members and is attached generally centrally thereof so that a gap is provided between the angle members and the upstanding flanges of the corner members.

With particular reference to FIGS. 4 and 7, a plurality of side wall sections 12 are provided and each of such side wall sections includes an outer panel 24 and an inner panel 25 separated by several upright studs 26. Preferably the panels 24 and 25 are constructed of sheet material such as stainless steel, Formica, or other material which may be easily cleaned and which does not give off pollutants. In most of the side wall sections, the outer and inner panels are imperforate and non-porous; however, the side wall sections that will be arranged along one side of the clean room 10 are provided with a plurality of openings in the inner panel, as illustrated in FIG. 7. In the perforated panels a first series of openings 27 are located adjacent to the bottom portion of each panel, a second series of openings 28 are disposed upwardly from the first series, a third series of openings 29 are located above and in spaced relationship with the second series of openings 28, and a fourth series of openings 30 are disposed adjacent to the upper end of the wall section. Preferably the openings 27 and 28 are of a similar size, while the openings 29 are of a smaller size, and the openings 30 are of a substantially larger size.

It is noted that if desired a grill (not shown) could be provided for each of the openings. Also it is noted that the series of openings could be replaced with elongated slots with the main requirement being that the openings provide communication into the space between the inner and outer panels.

The thickness of the side wall section is substantially equal to the width of the web portions of the base members so that the panels 24 and 25 are received between the flanges of such base members. Along the sides of each of the side wall sections a U-shaped reinforcing channel 31 is mounted and at least one of such reinforcing channels may be provided with a strip of flexible foam material 32 to close any gap between adjacent side wall sections. The reinforcing channel 31 is substantially the same size and configuration as the base members and therefore such reinforcing channel is spaced from the bottom of the side wall sections by a dimension equal to the height of the flanges of the base member so that the lower edge of the reinforcing channel substantially abuts the flanges of the base member. Also the upper end of each reinforcing channel is spaced downwardly from the upper end of the side wall sections for a purpose which will be described later.

When a first side wall section is applied to the base members, the end stud 26 of such wall section is received between the angle member 20 and the flange of the base member, and the intermediate stud 26 is received between the angle members 19 of the tie plate. When a second side wall section is placed on the corner member, the end stud 26 is received between the angle member 20 and the first side wall section, while the intermediate stud 26 is located between the angle members 19 of the tie plate 17 in the other direction.

After the side walls sections have been placed on the base members, one or more roof sections 13 are placed on the upper ends of the side wall sections and connected thereto. Each of the roof sections includes a top panel 33 and a bottom panel 34 which are disposed in spaced relationship with each other and are connected together by end walls 35 and 36 and side walls 37. In order to connect the roof sections 13 to the side wall sections 12, an inverted generally U-shaped yoke 38 is welded or otherwise fixed to each of the end walls 35 and 36. Each portion of the yoke 38 is generally U-shaped in cross-section and is of a size to receive the upper end of a side wall section 12 in such a manner that the downwardly extending arms of the yoke 38 substantially abut the upper end of the reinforcing channel 32 of the side wall section.

The top and bottom panels and the end and side walls of the roof section define a hollow compartment which is separated by a transverse partition 39 into an air return chamber 40 and a plenum chamber 41. The partition 39 has an opening 42 which communicates with an electrically operated blower 43 and such blower forces air under pressure from the air return chamber 40 into the plenum chamber 41. The end wall 36 of the roof section includes a plurality of openings 44 which are substantially in alignment with the openings 31 in the perforated side wall sections and provide a communication between the interior of the side wall section and the air return chamber 40.

Within the plenum chamber 41 the bottom panel 34 has a relatively large opening 45 around the periphery of which is located an downwardly extending flange 46. An air cleaner 47 is provided which includes a micro filter media 48 mounted within a frame 49 and such frame sealingly engages the flange 46 in such a manner that all of the air within the plenum chamber must pass through the filter media. The micro filter media may include a HEPA filter which captures approximately 99.97% of all airborne particles down to 0.3 micron diameter size so that the recirculated air being discharged through the filter media is classified as Class 100 air. A distribution panel 50 is located below the air cleaner 47 and is mounted within the opening 45 so that the air which is forced through the filter media is disbursed in a non-aspirating turbulence free flow.

A table or other work surface 51 is located within the clean room 10 directly below the distribution panel 50 and such work surface is supported at a convenient height in any desired manner, as by legs 52. In order to confine the clean air to a restricted area within the clean room and to insure that the air above the work surface remains clean, a transparent substantially distortion free partition 53 is suspended from the bottom panel 34 of the roof section in any conventional manner, as by hinges, clips or the like. The transparent partition 53 extends downwardly from the bottom roof panel and terminates at a predetermined distance above the work surface 51 so that the air from the distribution panel 50 flows downwardly to the work surface and then outwardly below the transparent partition. If desired one or more braces (not shown) are provided to hold the transparent partition 53 in fixed position.

In order to accommodate the side wall sections 12 on all sides of the clean room, a lefthand roof section and a righthand roof section must be provided. When the clean room is of a size greater than the width of the righthand and lefthand roof sections, one or more intermediate roofing sections may be inserted between such righthand and lefthand roof sections. As illustrated best in FIG. 1, each of the roof sections is substantially twice as long as it is wide and therefore a pair of yokes 38 are welded or otherwise attached to one of the side walls 37 of each of the righthand and lefthand roof sections. Such yokes are arranged in end-to-end abutting relationship and are adapted to receive the upper ends of the side wall sections 12 at each end of the clean room.

One of the side wall sections 12' is provided with a door 54 to permit access to the clean room and preferably such side wall section has an opening 55 directly above the door 54 so that in the event that the door is opened and clean air tends to escape from the clean room, at least a portion of the escaping air will be drawn back into the clean room through the opening 55 due to the partial vacuum within the air return chamber 40. If desired, such opening may be covered by a decorative grill or the like. Also, if desired, one or more fixed windows (not shown) may be provided in the side wall sections 12 to admit light to the clean room.

With particular reference to FIG. 2, the bottom panel 34 of each roof section in the area of the air return chamber 40 is provided with an opening 56 which is covered by the light unit 57 to provide interior lights for the clean room. Additional lights (not shown) may be provided for the table or work surface 51 to illuminate any object mounted thereon and to facilitate the operator's work.

As shown best in FIGS. 2 and 8, the side walls 37 of the roof sections 13 are provided with a plurality of openings 58 in the area of the air return chamber 40 so that when two or more roof sections are in abutting relationship, the air pressure in all of the air return chambers is equalized. Also, each of the interior side walls 37 of the roof sections is provided with a pair of longitudinally spaced openings 59 which receive mechanical fasteners such as clips 60 or the like to connect the roof sections together.

Further air heating, cooling and humidifying apparatus may be disposed within the air return chamber 40 for the comfort of the operators or when a controlled environment is required. Under some conditions, particularly when the air surrounding the exterior of the clean room is laden with pollutants, it may be desirable to insert a coarser, less expensive filter in the air return chamber 40 to prolong the life of the air cleaner 47.

Although the various elements which are used to construct the clean room may be of any desired size, a convenient size has been to provide the base portions with corner members the legs of which are approximately two feet long, and the intermediate channel members having a length of approximately four feet. The side wall sections are approximately eight feet high by four feet wide and a thickness of substantially four inches. The roof sections are approximately eight feet long by four feet wide and have a thickness or distance between the top and bottom panels of approximately twelve inches.

Figure 10:
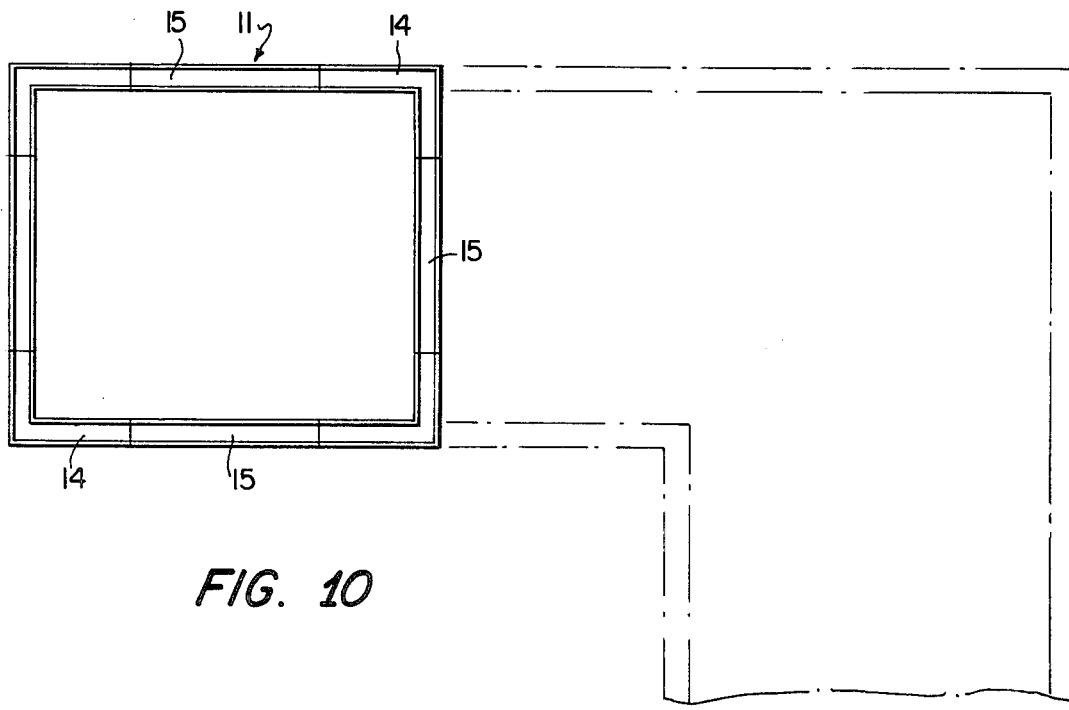
FIG. 10 is a schematic view illustrating the floor plan layout of a clean room.

In the operation of the device, the corner members 14 are placed on a relatively flat level floor of a large enclosure as illustrated in FIG. 10, and one or more intermediate channel members are located between the corners. After the corner members are aligned with the intermediate channel members and are arranged in a desired configuration, a tie plate 17 is positioned between the corner members and the adjacent intermediate channel members with the openings 18 of the tie plate receiving the pins 16 of the base members. The tie plate assists in maintaining the corner members and intermediate channel members in aligned abutting relationship with each other and prevents such members from moving apart. When the base has been assembled, the side wall sections 12 which will function as the ends of the clean room are placed on the base 11. One of the studs 26 of the side wall section is received between the angle members 20 and the corner and another stud 26 of the side wall is received between the angle members 19 of the tie plate. With this construction the side wall sections extend along the corner members 14 and to a position approximately one-half of the length of the intermediate channel member 15. A second side wall section 12 is placed on the base with one end of the second side wall section being in abutting relationship with the first side wall section. In this position, one of the end studs 26 of the second side wall section is received between the angle member 21 and the first side wall section, while the intermediate stud is received between the angle members 19 of the tie plate. Since the base members and side wall members are in staggered relationship with each other and since the lower ends of the side wall sections are received between the upstanding flanges of the base member, such elements are maintained in a straight line and are prevented from shifting laterally by the angle members 19, 20 and 21 in addition to the tie plate 17.

When all of the side wall sections have been placed on the base members, the roof sections 13 are raised to a position above the side wall sections and are lowered until the upper ends of the side wall sections are received within the yokes 38 of the roof sections. The inner and outer panels of the side wall sections along one side and both ends of the clean room are imperforate and the inner panels of the remaining side wall sections include a series of openings 27, 28, 29 and 30. When the roof sections 13 are mounted on the side wall sections, the openings 44 in the end wall 36 of the roof section must be in alignment with the openings 30 in the upper end of the side wall sections. Each of the roof sections 13 and, if desired, each of the side wall sections are prewired and are provided with terminal connectors so that when such sections are assembled such connectors are joined together. One of the sections has an electrical lead which is connected to a master relay control panel to provide electrical energy to the clean room 10.

After the clean room 10 has been erected, the work surfaces 51 are installed and then the partitions 53 are mounted in position suspended from the bottom panel of the roof sections. The smallest clean room that can be assembled is approximately eight feet square; however, additional units may be added in width increments of four feet. Preferably the first transparent partition 53 is approximately eight feet long and spans two roof sections, and additional transparent partitions 53 may be added in lengths of four and eight feet depending upon the number of roof sections in the clean room. When two or more transparent partitions are arranged in end-to-end relationship, the adjacent ends of such partitions are joined by a transparent connector which has a cross-section similar to an H.

Thereafter the blower 43 is operated and such blower removes air from the air return chamber 40 and forces such air under pressure into the plenum chamber 41 where the air passes through the air cleaner 47 and flows downwardly through the distribution panel 50 onto the work surface 51 and then is diverted outwardly below the transparent partition. Simultaneously the operation of the blower creates a partial vacuum in the air return chamber which causes air from the clean room to flow through the openings 27, 28 and 29 into the area between the outer and inner panels 24 and 25 of the perforated side wall sections and such air is vented through the openings 30 in the inner panel of the side wall section and the openings 44 in the end wall 36 of the roof section into the air return chamber. The openings 27, 28 and 29 are vertically spaced along the side wall section so that air is recirculated through substantially the entire clean room. Ideally the blower is operated at a speed to cause the air to pass below the partition at a rate of approximately 100 linear feet per minute and such air is continually recycled through the air cleaner.

Since the air always flows from the work surface past the operators, any contaminants given off by the operators are removed by the air cleaner before the air is introduced into the work area. Additionally any time that the door 54 is used for the ingress or egress of an operator, any air entering the room from the exterior must pass through the air cleaner prior to being introduced into the work area. Within the work area, the air flowing through from the plenum chamber through the distribution panel is at a pressure higher than atmospheric and therefore any leakage of air in the work area will result in air flowing out of the clean room which prevents the inflow of contaminated atmospheric air to the work surface.

If desired, the clean room may be provided with an anteroom at the end where the door is located in which case a transparent or other partition is disposed between the work area and the anteroom to prevent contaminated air from the anteroom entering the work area.

Although the clean room has been illustrated as being approximately eight feet wide and eight feet high with an indefinite length depending upon the number of units, it is contemplated that the room may be made larger in a transverse direction by placing additional intermediate channel members along the bases of the ends of the room, placing additional side wall sections along the base and then mounting two or more roof sections 13 in end-to-end abutting relationship. In order to support the ends of the roof section which do not engage the side wall sections, a post is provided having a plurality of clips or sockets at the upper end which receive the lower portions of the abutting yokes 38 of the roof sections. Since the posts are positioned at a location where four roof sections come together, each post supports the corners of all four roof sections. Normally when the clean room is expanded lengthwise of the roof sections, the work surfaces or tables 51 may be disposed either along opposite sides of the clean room, or such work surfaces may be disposed generally centrally of the room and in abutting relationship with each other depending upon the direction in which the roof sections 13 are mounted. In any event the air being discharged through the distribution panel onto the work surface is caused to flow away from the work surface and past any operators so that the air in the work area remains as Class 100 air.

We claim:

1. A prefabricated knockdown clean room for providing clean air to a work area comprising a plurality of independent base members located in end-to-end relationship, each of said base members being generally U-shaped in cross section and facing upwardly, a tie plate member bridging each pair of aligned base members, said tie plate members and said base members having interlocking means so that said tie plate members substantially prevent relative lateral and lengthwise movement of contiguous base members, a plurality of independent side wall sections vertically slidably received within said base members, each of said side wall sections having spaced inner and outer panels connected together by end walls, the inner panel of certain of said side wall sections being imperforate and the inner panel of at least one side wall section having at least one return opening therein to permit air within the clean room to enter the space between said inner and outer panels, sealing means attached to the exterior of at least one end wall of each side wall section and engagable with a contiguous side wall section, a roof section including top and bottom panels connected together by end walls and side walls and defining a hollow compartment, generally U-shaped yoke means on at least said end walls of said roof section for slidably receiving the upper portions of said side wall sections and detachably connecting said roof section and side wall sections together, a partition separating said compartment into a plenum chamber and an air return chamber, the space between said panels of said one wall section and said air return chamber being in communication with each other, blower means for moving air from said air return chamber into said plenum chamber, said bottom panel of said roof section having an opening into said plenum chamber, a micro filter extending entirely across said roof section opening so that air from said plenum chamber must be discharged through said micro filter, depending barrier means supported by said roof section adjacent to said roof section opening and extending entirely across said clean room, a work area located directly below said micro filter and said opening, air from said plenum chamber being directly introduced into said work area, said one of said side walls being remotely located from said work area so that the flow of clean air is maintained in a path from said plenum chamber into said work area and subsequently to the remaining portion of the interior of said clean room from which such air is returned to the plenum chamber by way of said one of said side walls and said air return chamber, whereby said base member, side wall sections and roof section may be easily assembled on a relatively flat surface to form a clean room.

2. The structure of claim 1 in which said base members include a plurality of right angle corner members and a plurality of relatively straight intermediate members.

3. The structure of claim 1 including upstanding members fixed to said corner members in a position to engage portions of said side wall sections and substantially prevent sidewise movement of said side wall sections relative to said base members.

* * * * *